United States Patent [19]

Yeager et al.

[11] Patent Number: 4,873,371

[45] Date of Patent: Oct. 10, 1989

[54] HYDROXY-TERMINATED ARYLENE ETHERS, AND METHOD FOR MAKING

[75] Inventors: Gary W. Yeager, Schenectady; David N. Schissel, Clifton Park, both of N.Y.

[73] Assignee: General Electric Company, Schnectady, N.Y.

[21] Appl. No.: 226,594

[22] Filed: Aug. 1, 1988

[51] Int. Cl.[4] ............................................. C07C 43/295
[52] U.S. Cl. ..................................... 568/33; 568/633; 568/637; 568/638
[58] Field of Search ................ 568/633, 638, 637, 33, 568/315, 433; 560/70, 131

[56] References Cited

PUBLICATIONS

*Russian Chemical Reviews*, 43(8), 1974, A. Moroz et al., "The Ullmann Ether Condensation", pp. 679–689.

*Organic Reactions*, C. Hassall, "The Baeyer–Villiger Oxidation of Aldehydes and Ketones", pp. 73–102.

"The Chemistry of the Diaryl Ethers", H. Ungnade, *Chem. Rev.*, 38 (1946), pp. 405–446.

*Primary Examiner*—Donald B. Moyer
*Assistant Examiner*—Karen E. Plue
*Attorney, Agent, or Firm*—William A. Teoli; James C. Davis, Jr.; James Magee, Jr.

[57] ABSTRACT

A method is provided for making certain hydroxy-terminated arylene ethers useful as spacers in liquid crystalline polyesters. There is initially formed a dicarbonyl adduct from a dihydroxyaromatic compound, such as hydroquinone and a haloarylcarbonyl compound. The adduct formed is oxidized to the corresponding diester. Hydrolysis of the diester provides the hydroxy-terminated arylene ether.

10 Claims, No Drawings

HYDROXY-TERMINATED ARYLENE ETHERS, AND METHOD FOR MAKING

BACKGROUND OF THE INVENTION

The present invention is directed to a method for making certain hydroxy-terminated arylene ethers, such as 4,4'[arylbis(oxy)]bisphenols included within the formula, $$HO-R^1-O-R-O-R^1-OH, \quad (1)$$

where R is a member selected from the class consisting of $C_{(6-36)}$ arylene groups and $C_{(6-36)}$ arylene groups substituted with monovalent radicals inert during hydroxy-terminated arylene-forming reactions, $R^1$ is a member selected from the class consisting of $C_{(6-20)}$ divalent arylene radicals and $C_{(6-20)}$ divalent arylene radicals substituted with monovalent radicals inert during hydroxy-terminated arylene ether-forming reactions. The hydroxy-terminated arylene ethers of formula (1) are made from certain dihydroxyaromatic compounds defined below. The hydroxy-terminated arylene ethers of formula (1) are useful as flexible spacers in liquid crystalline aromatic polyesters.

Prior to the present invention, certain 4,4'[arylbis(oxy)]bisphenols included within formula (1) were prepared by the copper catalyzed Ullmann condensation of 4-methoxyphenol with a dihaloaromatic compound followed by demethylation of the resulting bismethyl ether. A less commonly used procedure for the preparation of 4,4'[arylbis(oxy)]bisphenols is the Ullmann condensation of 1-bromo-4-methoxybenzene with a dihydroxyaromatic compound followed by demethylation of the resulting bismethyl ether. The advantage of the second method is that readily available dihydroxyaromatic compounds can be used as starting materials.

SUMMARY OF THE INVENTION

The present invention is based on the discovery that the hydroxy-terminated arylene ethers included within formula (1), can be made by a three-step procedure involving (1) treating a dihydroxyaromatic with a benzophenone or benzaldehyde having a leaving group in the para position selected from the class consisting of fluoro, bromo, and nitro in the presence of a phenol deprotonating agent and a substantially inert organic solvent to form the corresponding bis(arylene)ether, (2) effecting a Baeyer-Villiger oxidation of the bis-(arylene)ether of step (1) in the presence or absence of a catalytic amount of an alkylsulfonic acid to provide the corresponding arylene etherdiester, and (3) saponifying the arylene etherdiester of step (2) to form a hydroxy-terminated arylene ether included within formula (1).

STATEMENT OF THE INVENTION

There is provided by the present invention, a method for making hydroxy-terminated arylene ethers of formula (1) comprising, (1) effecting reaction between a dihydroxyaromatic compound and an arylcarbonyl compound having a leaving group in the para position selected from fluoro, bromo, and nitro to form an arylene ether dicarbonyl adduct of the formula, $$XC(O)-R^1-O-R-O-R^1-C(O)X, \quad (2)$$

(2) oxidizing the resulting arylene ether dicarbonyl adduct of step (1) to form the corresponding arylene ether diester, of the formula, $$XCO-R^1-O-R-O-R^1-OCX, \quad (3)$$

(with both carbonyls as shown)

(3) saponifying the arylene ether diester of step (2) to form the corresponding hydroxy-terminated arylene ether of formula (1),
where R, and $R^1$ are as previously defined, and X is a member selected from the class consisting of hydrogen, a $C_{(6-14)}$ arylene group, and halogenated derivatives thereof.

Radicals included by R of formulas (1)-(3) are, for example, phenylene, tolylene, biphenylene, chlorophenylene, naphthalene, etc., and radicals included by the formula, $$-R^2-(Q)_a-R^2-,$$

where $R^2$ is a $C_{(6-14)}$ divalent aromatic radical selected from hydrocarbon radicals and halogenated hydrocarbon radicals, and Q is a divalent organo radical selected from

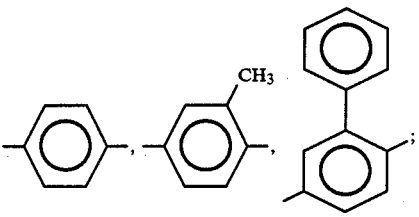

where a is 0 or 1, y is an integer having a value from 1-5 inclusive, and $R^3$ is monovalent hydrocarbon radical selected from methyl or phenyl.

Radicals included in $R^1$ are, for example,

Inert radicals which can be chemically bound to R and $R^1$ are preferably halo, such as chloro, and $C_{(1-8)}$ alkyl such as methyl. Radicals included within X of formula (3) are, for example, phenyl, tolyl, xylyl, and chlorophenyl.

Dihydroxy aromatic compounds, which can be used in the practice of the present invention to make the hydroxy-terminated arylene ethers of formula (1), are compounds included within the following formula, $$HOR-OH, \quad (4)$$

where R has been previously defined. Some of these dihydroxyaromatic compounds which can be used in the practice of the present invention are, for example, hydroquinone, 4,4'-oxydiphenol, 4,4'-biphenol, 6,6'- dihydroxy-3,3,3',3'-tetramethyl-1,1'-spirobiindane, 2,6-dihydroxynapthalene, and 4,4'-(1-methylethylidene)bisphenol.

Phenol deprotonating agents which can be used in the practice of the present invention are, for example, alkali or alkaline earth metal carbonates, or hydroxides, such as potassium carbonate, sodium or potassium hydroxides, magnesium carbonate, etc. Choice of a particular deprotonating agent will be influenced by the organic solvent used and its solubility therein.

Oxidizing agents which can be used to convert the arylene ether dicarbonyl adduct of formula (2) to the corresponding diester are, for example, peroxides such as 3-chloroperoxybenzoic acid, hydrogen peroxide, performic acid, peracetic acid, etc.

Substantially inert organic solvents which can be used are, for example, dipolar aprotic solvents such as dimethyl acetamide, N-methylpyrollidinone, dimethylformamide, and dimethylsulfoxide.

In the practice of the preferred form of the present invention, reaction is effected between the dihydroxyaromatic compound of formula (4) and a fluoroarylaldehyde, such as 4-fluorobenzaldehyde in the presence of an anhydrous alkali metal carbonate, such as potassium carbonate, and a dipolar aprotic solvent, such as dimethylacetamide.

Alternatively, there can be used a fluoroarylketone, such as 4-fluorobenzophenone if desired. There is produced an arylene ether dicarbonyl adduct of formula (2), such as the corresponding bis(4-formylphenyl)ether, where X is hydrogen or bis(4-benzoylphenyl)ether where X is phenyl.

Oxidation of the arylene ether dicarbonyl adduct of formula (2) can be achieved with 3-chloroperoxybenzoic acid in the presence or absence of a catalytic amount of an alkanesulfonic acid, such as methanesulfonic acid to produce the corresponding arylene ether diester, such as the bis(4-formyloxyphenyl)ether derivative or bis(4-benzoyloxyphenyl)ether derivative.

The hydroxy-terminated arylene ether of formula (1) can be made by saponifying the resulting arylene ether diester of formula (3) with an alkali metal hydroxide solution, such as a methanolic KOH solution.

The hydroxy-terminated arylene ethers of the present invention can be used as flexible spacers in the production of aromatic polyesters exhibiting anisotropic properties in the molten state.

The following examples are given by way of illustration and not by way of limitation. All parts are by weight.

EXAMPLE 1

There was added 41.5 grams (0.30 mole) of anhydrous potassium carbonate to a solution of 11 grams (0.10 mole) of hydroquinone, 24.8 grams (0.20 mole) of 4-fluorobenzaldehyde and 200 ml of dimethylacetamide. The resulting solution was heated at reflux for 12 hours. The reaction mixture was then decanted from the insoluble potassium salts and allowed to cool. The cooled solution was added to water to effect precipitation of product which was isolated by filtration. The product was recrystallized from isopropanol/water to yield 21 grams (66%) of 4,4'[1,4-phenylenebis(oxy)]bisbenzaldehyde having a melting point of 157°–158° C. The identity of the product was further confirmed by proton NMR.

A solution of 15.92 grams (0.05 mole) of the above bisbenzaldehyde and 150 ml of chloroform was treated while it was stirred with 21.57 grams (0.125 mole) of 3-chloroperoxybenzoic acid over a period of 10 minutes. After one hour, the solvent was evaporated and the resulting solids slurried with 150 ml of cold methanol. The solution was filtered and the filter cake washed with methanol. The isolated solid was dried in vacuo to provide 14.4 grams (82%) of 4,4'[1,4-phenylenebis(oxy)]bisphenol diformate. Structure was confirmed by proton NMR.

A solution of 60 grams (0.65 mole) of potassium hydroxide in 100 ml of methanol was added with stirring at room temperature to a solution of 10.5 grams (0.03 mole) of the above bisphenoldiformate and 50 ml of methanol. The resulting mixture was stirred for one hour at room temperature. The methanol was then evaporated and the resulting solid dissolved in a minimal amount of water. Upon acidification, a solid precipitated from the solution. The resulting precipitate was filtered and there was obtained 8.21 grams (0.028 mole), or 93% of product. Based on $^1$H-NMR, method of preparation, the product was 4,4'-[1,4-phenylenebis(oxy)]-bisphenol of the formula,

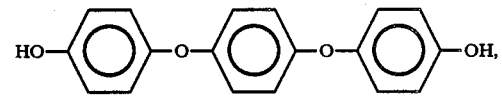

The above procedure was repeated except that in place of hydroquinone which provided "a" in Table I below, there was used several additional dihydroxyaromatic compounds included within formula (4), where R is a member selected from

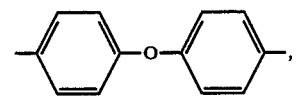
b

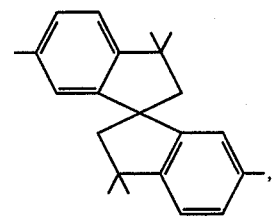
c

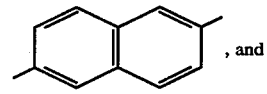
d
, and

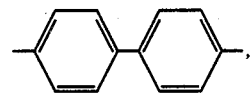
e which correspond to the other hydroxy-terminated arylene ethers of Table I. The following results were obtained, where "Compounds" means hydroxy-terminated arylene ethers:

TABLE I

| Compounds | Recrystallization Solvent | mp °C.* | $^1$H-NMR (DMSO/TMS, 90 MHz), δ |
|---|---|---|---|
| a | Toluene | 188–189 | 6.67–7.00 (m, 12H), 9.30 (broad s, 2H) |
| b | Toluene | 195–197 | 6.70–7.20 (m, 16H), 9.37 (broad s, 2H) |
| c | Toluene | 205.5–210 | 1.30 (s, 12H), 2.26 (q, 4H), 6.27 (d, 2H), 6.65–6.91 (m, 12H), 7.20 (d, 2H), 9.3 (broad s, 2H) |
| d | Toluene | 170–172 | 6.23 (broad s, 2H), 6.78–7.10 (m, 4H), 7.13–7.40 (m, 4H), 7.70–7.90 (d, 2H) |
| e | Toluene | 231–234 | 6.73–7.13 (m, 12H), 7.60 (d, 4H) 9.43 (broad s, 2H) |

*Melting points are uncorrected.

EXAMPLE 2

A mixture of 40.01 grams (0.2 mole) of 4-fluorobenzophenone, 11.01 grams (0.1 mole) of hydroquinone, and 500 ml of dimethylsulfoxide was stirred until the solids had dissolved. There was then added 41.46 grams (0.3 mole) of anhydrous potassium carbonate. The solution was then heated at 135°–155° C. for 50 hours. The mixture was then treated with 200 ml of cold water. A solid precipitated which was filtered and recrystallized from orthodichlorobenzene. There was obtained 38.8 grams (0.87 mole) or an 87% yield of product. Based on $^1$H-NMR and the method of preparation, the product was 4,4'[1,4-phenylenebis(oxy)]bisbenzophenone.

A mixture of 22.3 grams (0.05 mole) of the above arylene ether bisbenzophenone, 25.8 grams (0.15 mole) of 3-chloroperoxybenzoic acid, 400 ml of chloroform, and 1 ml of methanesulfonic acid was stirred at room temperature for 70 hours. The solid was then evaporated and the resulting solid was slurried in 150 ml of methanol. The solution was filtered and the filter cake washed with methanol. The isolated solid was dried overnight in a vacuum oven to provide 25.1 grams of crude product. The isolated product was recrystallized from a minimal amount of dimethylsulfoxide to yield 17.8 grams (0.043 mole) or 86% yield of the product. Based on $^1$H-NMR and the method of preparation, the product was 4,4'[1,4-phenylenebis(oxy)]bisphenol dibenzoate.

A solution of 2.46 grams (0.044 mole) of potassium hydroxide and 100 ml of methanol was added to a solution of 4.78 grams (0.01 mole) of the above dibenzoate in 50 ml of methanol. The resulting solution was refluxed for three hours. The solvent was then evaporated and the resulting solid dissolved in 100 ml of water and acidified to pH~1 with concentrated HCl. The resulting precipitate was isolated by filtration, and dried overnight in a vacuum oven. The crude product was recrystallized from toluene to provide 2.9 grams (9.86 millimole) or 98.6% yield of product. Based on the characterization data in Table II below and the method of preparation, the product was 4,4'[1,4-phenylenebis(oxy)]bisphenol.

Following the same procedure, dihydroxy-aromatic compounds within the scope of formula (4) were converted to hydroxy-terminated arylene ethers. Some of the dihydroxyaromatic compounds were the same dihydroxyaromatic compounds used to make compounds "a–c", shown for Example 1. Additional dihydroxyaromatic compounds were also used, where R is f and g, within the scope of formula (4), as follows:

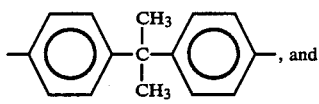, and

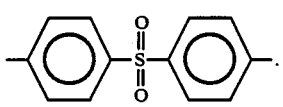.

The following results were obtained, where compounds a, b, and c are the same as shown in Table I, and "IPA" is isopropanol:

TABLE II

| Compounds | Recryst. Solvent | mp, °C.* | $^1$H-NMR (D$_6$-DMSO/TMS, 90 Hz), δ |
|---|---|---|---|
| a | Toluene | 181–182 | 6.80 (broad s,8H), 6.89 (s,4H), 9.25 (s,2H) |
| b | IPA/H$_2$O | 196–198 | 6.63–7.10 (m,16H), 9.20 (s,2H) |
| c | Toluene | 189–191 | 1.13–1.47 (s,12H), 2.23 (dd,4H), 6.23 (d,2H), 6.47 (broad s,12H) 6.97–7.29 (m,4H), 9.20 (s,2H) |
| f | — | oil | 1.70 (s,6H), 6.63–6.89 (m,12H), 7.12 (d,4H) |
| g | Toluene | 172–174 | 6.69–7.22 (m,12H), 7.90 (d,4H) 9.75 (broad s,2H) |

*Uncorrected

Certain of the above hydroxy-terminated arylene ethers were respectively converted to the corresponding diacetates and then separately intercondensed with acetoxybenzoic acid, hydroquinonebisacetate, and terephthalic acid to form polyesters. The respective polyesters were found to display anisotropic properties when examined with a hot-stage polarized light microscope.

Although the above examples are directed to only a few of the very many hydroxy-terminated arylene ethers of the present invention, it should be understood that the present invention is directed to a much broader variety of hydroxy-terminated arylene ethers as shown in the description preceding these examples.

What is claimed and sought to be protected by Letters Patent of the United States is as follows:

1. A method for making a hydroxy-terminated arylene ether of the formula

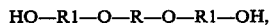

comprising,
(1) reacting a dihydroxyaromatic compound of the formula,

and with an arylcarbonyl compound selected from aldehydes and ketones having a leaving group in the para position, selected from fluoro, bromo, and nitro to form an arylene ether dicarbonyl adduct of the formula,

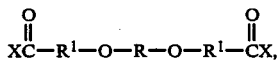

(2) oxidizing the resulting arylene ether dicarbonyl adduct of step (1) to form the corresponding arylene ether diester of the formula,

(3) saponifying the arylene ether diester of step (2) to the corresponding hydroxy-terminated arylene ether, where R is a substituted or unsubstituted arylene radical having from 6–36 carbons, $R^1$ is the same or different arylene radical having from 6–20 carbons and X is hydrogen or an arylene group having from 6–14 carbons.

2. A method in accordance with claim 1, where the arylcarbonyl compound is 4-fluorobenzaldehyde.

3. A method in accordance with claim 1, where the arylcarbonyl compound is 4-fluorobenzophenone.

4. A method in accordance with claim 1, where R is

5. A method in accordance with claim 1, where R is

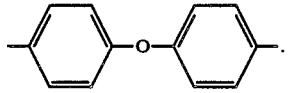

6. A method in accordance with claim 1, where R is

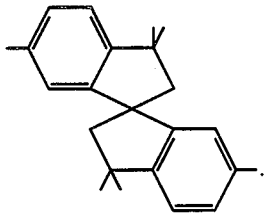

7. A method in accordance with claim 1, where R is

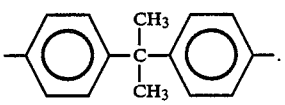

8. A method in accordance with claim 1, where R is

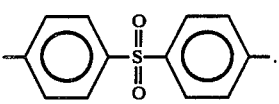

9. A method in accordance with claim 1, where R is

10. A method in accordance with claim 1, where R is

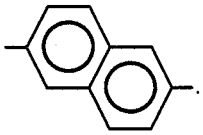

* * * * *